United States Patent [19]
Zucker

[11] Patent Number: 5,324,634
[45] Date of Patent: Jun. 28, 1994

[54] DIAGNOSTIC TESTS MEASURING GELATINASE/INHIBITOR COMPLEXES FOR DETECTION OF AGGRESSIVE AND METASTATIC CANCER

[75] Inventor: Stanley Zucker, Hauppauge, N.Y.

[73] Assignee: The Research Foundation of State University of New York, Albany, N.Y.

[21] Appl. No.: 860,901

[22] Filed: Mar. 31, 1992

[51] Int. Cl.$^5$ ............... G01N 33/574; C12Q 1/37
[52] U.S. Cl. ................... 435/7.23; 435/7.92; 435/7.94; 435/23; 436/518
[58] Field of Search ........... 435/7.23, 7.92, 7.94, 435/23, 810; 436/518; 530/387.1, 388.1

[56] References Cited

U.S. PATENT DOCUMENTS

| | | |
|---|---|---|
| 4,424,278 | 1/1984 | Bucovaz et al. |
| 4,584,268 | 4/1986 | Ceriani et al. |
| 4,628,027 | 12/1986 | Gay |
| 4,677,058 | 6/1987 | Tryggvason et al. |
| 4,690,890 | 9/1987 | Loor et al. |
| 4,693,969 | 9/1987 | Saxena et al. |
| 4,808,528 | 2/1989 | Tryggvason et al. |
| 4,816,400 | 3/1989 | Tryggvason et al. |
| 4,837,145 | 6/1989 | Liotta |
| 4,871,834 | 10/1989 | Matsuoka et al. |
| 4,882,268 | 11/1989 | Penman et al. |
| 4,885,236 | 12/1989 | Penman et al. |
| 4,914,021 | 4/1990 | Toth et al. |
| 4,929,544 | 5/1990 | Vold |
| 4,931,386 | 6/1990 | Silver et al. |

FOREIGN PATENT DOCUMENTS

WO90/10062 1/1990 PCT Int'l Appl.

OTHER PUBLICATIONS

Akaza et al., "Analysis of Cell Surface Antigens of Gastric Cancer and Preliminary Study of Clinical Application by Using Mouse Monoclonal Antibodies Produced Against NUGC3", Abstract from *Nippon Geka Gakkai Zasshi*, 86 (4), 455-463 (1985).

Zucker et al., "Diversity of Human Pancreatic Cancer Cell Proteinases: Role of Cell Membrane Metalloproteinases in Collagenolysis and Cytolysis", *Cancer Research*, 45, 6168-6178 (1985).

Grigioni et al., "Behavior of Basement Membrane Antigens in Gastric and Colorectal Cancer", *Acta Pathol. Jpn.*, 36 (2), 173-184 (1986).

Carmichael et al., "Primary Structure and cDNA Cloning of Human Fibroblast Collagenase Inhibitor", *Proc. Natl. Acad. Sci. USA*, 83, 2407-2411 (1986).

Zucker et al., "Metastatic Mouse Melanoma Cells Release Collagen-Gelatin Degrading Metalloproteinases as Components of Shed Membrane Vesicles", *Biochimica et Biophysica Acta*, 924, 225-237 (1987).

Zucker et al., "Enrichment of Collagen and Gelatin Degrading Activities in the Plasma Membranes of Human Cancer Cells", *Cancer Research*, 47, 1608-1614 (1987).

Zucker et al., "Purification and Characterization of a Connective-Tissue-Degrading Metalloproteinase from the Cytosol of Metastatic Melanoma Cells", *Biochem. J.*, 245, 429-437 (1987).

Zucker, "A Critical Appraisal of the Role of Proteolytic Enzymes in Cancer Invasion: Emphasis on Tumor Surface Proteinases", *Cancer Investigation*, 6 (2), 219-231 (1988).

Birkedal-Hansen et al., "Monoclonal Antibodies to Human Fibroblast Procollagenase. Inhibition of Enzymatic Activity, Affinity Purification of the Enzyme, and Evidence for Clustering of Epitopes in the $NH_2$--Terminal End of the Activated Enzyme", *Biochemistry*, 27, 6751-6758 (1988).

(List continued on next page.)

*Primary Examiner*—Toni R. Scheiner
*Attorney, Agent, or Firm*—Hoffmann & Baron

[57] ABSTRACT

Diagnostic agents and methods for detecting the presence of metastatic activity in biological samples such as plasma are disclosed. The agent and method preferably immunologically detect matrix metalloproteinases in complexed form with endogenous inhibitors of MMP's. A kit for detecting the metalloproteinases is also disclosed.

11 Claims, 1 Drawing Sheet

OTHER PUBLICATIONS

Spinucci et al., "Purification of a Gelatin-Degrading Type IV Collagenase Secreted by ras Oncogene-Transformed Fibroblasts", *J. Natl. Cancer Inst.*, 80 (17), 1416–1420 (1988).

Stetler-Stevenson et al., "Tissue Inhibitor of Metalloproteinase (TIMP-2)", *J. Biol. Chem.*, 264 (29), 17374–17378 (1989).

Bergmann et al., "Enzyme Linked Immunosorbent Assays (ELISA) for the Quantitative Determination of Human Leukocyte Collagenase and Gelatinase", *J. Clin. Chem. Clin. Biochem.*, 27, 351–359 (1989).

Vartio et al., "Human Gelatinase/Type IV Procollagenase is a Regular Plasma Component", *FEBS Letters*, 225 (2), 285–289 (1989).

Zucker et al., "Gelatin-Degrading Type IV Collagenase Isolated from Human Small Cell Lung Cancer", *Invasion and Metastasis*, 9, 167–181 (1989).

Zucker et al., "Extraction of Type-IV Collagenase/Gelatinase from Plasma Membranes of Human Cancer Cells", *Int. J. Cancer*, 45, 1137–1142 (1990).

Cooksley et al., "Immunosassays for the Detection of Human Collagenase, Stromelysin, Tissue Inhibitor of Metalloproteinases (TIMP) and Enzyme-Inhibitor Complexes", *Matrix*, 10, 285–291 (1990).

Moll et al., "Tumor Promoter-Stimulated $M_r$ 92,000 Gelatinase Secreted by Normal and Malignant Human Cells: Isolation and Characterization of the Enzyme from HT1080 Tumor Cells", *Cancer Research*, 50, 6162–6170 (1990).

Moll et al., "Localization of Collagenase at the Basal Plasma Membrane of a Human Pancreatic Carcinoma Cell Line", *Cancer Research*, 50, 6995–7002 (1990).

Wacher et al., "Development of a Novel Substrate Capture Immunoassay for the Detection of a Neutral Metalloproteinase Capable of Degrading Basement Membrane (Type IV) Collagen", *Journal of Immunological Methods*, 126, 239–245 (1990).

Zucker et al., "Detergent Extraction and Characterization of Tumor Hemolytic Factor from Plasma Membranes of Oncogene Transformed Fibroblasts", *Int. J. Cancer*, 47, 274–280 (1991).

Zucker et al., "Proteinase-Alpha$_2$ Macroglobulin Complexes are not Increased in Plasma of Patients with Cancer" *Int. J. Cancer*, 48, 399–403 (1991).

Diagnostic Tests Measuring Gelatinase/Inhibitor Complexes for Detection of Aggressive and Metastatic Cancer

BACKGROUND OF THE INVENTION

The present invention relates to improvements in the diagnosis of metastic disease. In particular, the invention relates to techniques for detecting the presence of proteolytic enzymes associated with metastatic disease.

Although a cure for most forms of cancer remains elusive, early detection and treatment have historically provided the best prognosis. Considerable effort over the years has been directed to developing diagnostic tests which give an indication of the presence of metastatic disease at an early stage.

Recently, a relationship between matrix metalloproteinases (MMP's) and metastasis has been suggested. MMP's are a family of closely related metal-dependent endopeptidases secreted by mesenchymal cells. For example, gelatinase A (MMP-2 or 72 kDa gelatinase/type IV collagenase) and gelatinase B (MMP-9 or 92 kDa gelatinase/type IV collagenase) have been identified as playing a major role in cancer invasion and metastasis. Stromelysin and PUMP (Putative Metalloproteinase), metalloproteinases with broader substrate specificity, are also thought to participate in the metastatic process. Three of these metalloproteinases have been identified in mammalian plasma.

Metastasis is a complex sequence of events in which malignant cells detach and disseminate from a primary tumor. The malignant cells invade adjacent tissue, penetrate into blood and lymphatic vessels, circulate to distant sites and eventually attach to and penetrate tissues in distant organs, thereby proliferating the malignancy. An important part of the metastatic process is the degradation of extracellular basement membranes by various proteolytic enzymes. Basement membranes are collagen-containing connective tissues which form a tough continuous sheet and separate the various cell layers such as the epithelial, endothelial and parenchymal cells from interstitial connective tissue.

Proteolytic enzymes associated with the metastatic process are found circulating in the form of activated enzyme (free enzyme), latent free enzyme and enzyme complexed with endogenous proteinase inhibitors. Only the active forms, however, digest the connective tissue substrates. The body's own natural defense mechanisms rapidly inactivate MMP's by complexing the enzymes with specific tissue inhibitors of metalloproteinases (TIMP's). Such inhibitors found in the tissues and circulating in the plasma include TIMP-1, TIMP-2 and also alpha-2 macroglobulin which is primarily in blood.

In spite of the relationship between elevated levels of certain destructive proteases and the presence of metastatic disease, it has been difficult to use the relationship to provide an accurate indication of metastatic disease. In the past, it has only been possible to detect free or activated forms of the metalloproteinases, leaving a substantial portion of the inactivated enzymes complexed with inhibitors undetected. Recently it has been shown, however, that latent gelatinase A forms complexes with TIMP-2 and latent gelatinase B forms complexes with TIMP-1. Thus, these gelatinases can exist outside the cell in complexed forms with TIMPs.

U.S. Pat. No. 4,677,058 discloses purifying and detecting type IV collagenase antigens from malignant tumor cells. Similarly, U.S. Pat. No. 4,808,528 discloses antibodies specific to type IV collagenase enzyme antigens. U.S. Pat. No. 4,816,400, a division of the '058 U.S. Pat. No., supra, discloses immunological determination of type IV collagenase antigens using polyclonal and monoclonal antibodies. None of these references, however, disclose detecting collagenase enzyme-inhibitor complexes associated with metastatic disease.

In spite of the investigation of the role of metalloproteinases in metastatic disease, the total amount of MMP's being released and thus the actual metastatic activity has not been detectable. Indeed, due to the usually rapid inactivation of activated MMP's by TIMP's, measuring only free, circulating MMP's would fail to indicate the presence of many underlying diseases. Determining whether or not the complexes formed between MMP's and TIMP's form more reliable and sensitive diagnostic tests has yet to be investigated.

It is therefore an object of the present invention to provide highly specific and reliable diagnostic agents and methods to determine the presence of metastatic disease based on measuring matrix metalloproteinase inhibitor complex levels.

Other and further objects and advantages of the present invention will become apparent to those skilled in the art from a consideration of the following description taken together with the accompanying figure.

SUMMARY OF THE INVENTION

The present invention includes diagnostic agents and methods useful in the detection of metastatic activity in biological samples such as human plasma. The invention includes a first substance capable of immunologically reacting with enzymes broadly described as matrix metalloproteinases (MMP's). Such MMP's include gelatinase A (72 kDa type IV collagenase/gelatinase (MMP-2), gelatinase B (92 kDa type IV collagenase/gelatinase (MMP-9)), stromelysin (MMP-3), putative metalloproteinase (PUMP), partial breakdown products of these proteins and combinations thereof. The invention further includes a second substance which is immunologically reactive with endogenous inhibitors of the tissue-degrading enzyme metalloproteinases or TIMP's.

The first immunologically-reactive substance is preferably a monoclonal antibody having specificity for one or more MMP enzymes or circulating breakdown products of MMPs. Examples of such antibodies include monoclonal murine anti-MMP-2, monoclonal murine anti-MMP-9 and monoclonal murine anti-MMP-3, as set forth by Bergmann, et al. J. Clin. Chem. Clin. Biochem 27, 351–359 (1989) or Cell Tech Lmt. (Slough, England). Alternatively, antibodies such as rabbit polyclonal antibodies to native MMP's or peptide components such as peptide sequences of the native MMP's may be used.

The second immunologically responsive substance is preferably an antibody having specificity for endogenous inhibitors of MMP's, TIMP's or other associated proteins which bind to MMP's in plasma or tissue. For example, polyclonal rabbit anti-TIMP-1 or polyclonal anti-TIMP-2 as described by Carmichael, et al. Proc. Natl. Acad Sci. USA, 83:2407-2411 (1986) or the N.I.H. (Bethesda, MD) are examples of such substances. Alternatively, monoclonal antibodies to TIMP's may be selected.

The present invention also includes a method of detecting metastatic activity in a biological sample and a diagnostic kit. The method includes contacting a diagnostic agent such as that set forth above, with the biological sample and measuring the total amount of matrix metalloproteinases present and TIMP complexes uncovered to determine whether metastatic disease is present.

The diagnostic agent, method and kit of the present invention can be included as part of various immunoassay techniques, particularly ELISA and most preferably sandwich-type ELISA assays. Alternative immunoassay techniques such as immunoblotting, immunofluorescent, radio-immunoassay, fluorescence detection and/or enzyme assay methods are also contemplated.

As a result of the present invention, significantly more accurate determinations of metastatic activity are obtained by detecting not only free metalloproteinases and breakdown products of MMP's, but also complexes of the enzymes formed with inhibitors. This is a dramatic improvement over methods which only detect free or activated MMP's and completely missed those enzymes complexed to the inhibitor molecules. In addition, the assays described herein provide independent verification of disease. Thus, the results provided can supplement other tests and provide additional data not obtained with other tests.

For a better understanding of the present invention, reference is made to the following description, taken together with the accompanying figure, and its scope will be pointed out in the appended claims.

DETAILED DESCRIPTION OF THE INVENTION

Figure 1:
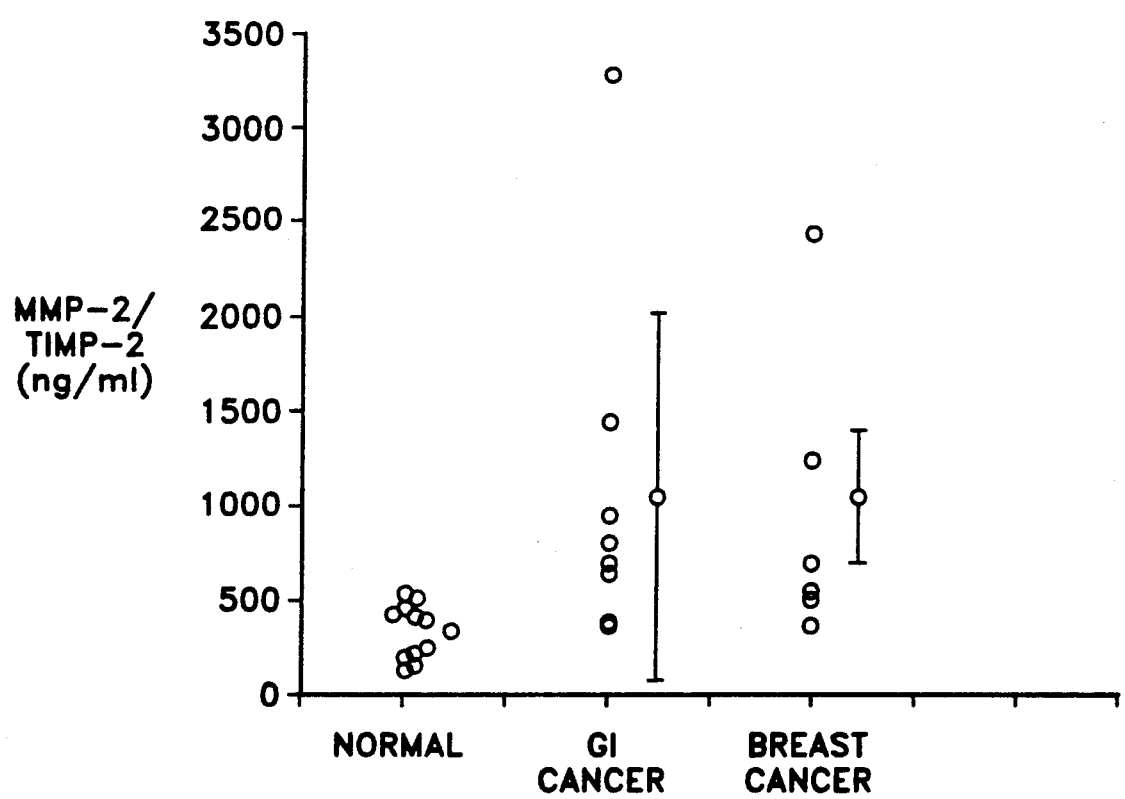
FIG. 1 graphically demonstrates the results of immunological assays carried out using sandwich-type ELISA techniques to detect metastatic activity in patients using the present invention.

The diagnostic agent and method of the present invention are based on the premise that high levels of certain metalloproteinases complexed to TIMP's in clinical samples strongly correlate with an underlying metastatic disease. Thus, while not necessarily indicating a particular type of cancer, the diagnostic agent and method of the present invention provide a means of indicating or affirming the presence of underlying metastatic disease in the biological fluids of suspected patients.

Blood and/or plasma are the most common biological sample assayed for diagnostic tests. Forpurposes of the present invention, the term biological sample small also include but not be limited to plasma, serum, tissue samples, aspirates, urine and tissue fluids. It is contemplated that the inventive diagnostic agent and method provide an indication of metastatic activity from any sample containing metalloproteinases in both free and complexed form, even in amounts as low as the nanogram per milliliter level.

The identification of metalloproteinases in clinical samples is preferably carried out using immunological techniques. The immunological techniques center around the the use of specific antibody-antigen reactions which indicate a response to only specific antigens, in particular, those enzymes associated with metastatic disease. Within this genre of tissue-degrading enzymes are gelatinase A (72 kDa type IV collagenase/-gelatinase (MMP-2)), gelatinase B (92 kDa IV collagenase/gelatinase (MMP-9), stromelysin (MMP-3), putative metalloproteinase (PUMP's), and break down products of the proteinases and combinations thereof. For diagnostic purposes, it is of importance to note that the recognition of these antigenic substances is in both the free and complexed form.

In order to achieve this result, the invention includes a first substance having immunospecificity to free metalloproteinases and complexed metalloproteinases. In a preferred embodiment, monoclonal antibodies are prepared to have the desired immunospecificity. For example, monoclonal antibodies may be obtained from hybridomas obtained from mice immunized by injection of 72 kDa progelatinase/type IV procollagenase purified from human fibroblasts. See Birkedal-Hansen, et al. Biochemistry 27, 6751–6758 (1988). It is essential that the antibody bind to the specific metalloproteinases when it is complexed to TIMP. Many antibodies currently used can recognize free metalloproteinase, but they fail to bind to MMP in complexes with inhibitors as described in more detail below. A non-limiting list of suitable antibodies include murine monoclonal anti-human 72 kDa or 92 kDa type IV collagenase/gelatinase antibodies, or murine monoclonal antibodies to stromelysins. One method of producing these antibodies which recognize MMPs in complexes is to use MMP-TIMP complexes as the immunogen in mice or rabbits.

The inventive diagnostic agent also includes a second substance having particular specificity for the naturally-occurring tissue inhibitors of metalloproteinases including TIMP-1, TIMP-2, and alpha macroglobulin. These antibodies need to be reactive to TIMPs in complexes with MMPs.

Free TIMP-1 has a molecular weight of 28 kDa, but in complexes with MMPs it is identified as approximately 95 kDa. Free TIMP-2 has a molecular weight of 22 kDa, but complexed with MMPs, it is identified as multiple components with molecular weights between 23 kDa 150 kDa. Because gelatinase A and gelatinase B breakdown to over time following activation or enzyme digestion, it is anticipated that lower molecular weight products of these MMPs may circulate in complexes with TIMPs. The molecular weights of TIMPs in plasma have been identified using immunoblotting techniques of non-reduced SDS-PAGE polyacrylamide gels.

Preferably, antibodies which achieve the necessary binding to complexed TIMP are prepared specific to MMP-TIMP complexes found in the biological sample. For example, polyclonal antibodies to human progelatinase/pro-type IV collagenase can be produced in rabbits by laboratory procedures known in the art. A good source for the immunogens is to isolate MMP-TIMP complexes from human plasma using gelatin Sephrarose chromatography to bind these antigens and dimethyl sulfoxide to elute the complexed proteins from the solid phase. These antigens are mixed with Freund's Adjuvant to enhance antibody response and are injected subcutaneously in rabbits on 3–5 occasions over a period of 4–6 weeks. Further examples of such polyclonal antibodies include rabbit anti-TIMP-1, rabbit anti-TIMP-2 and rabbit anti-alpha-2-macroglobulin. Suitable antibodies are also available from commercial laboratories such as Cell Tech Lmt. (Slough, England).

In an alternative embodiment, monoclonal antibodies are prepared with specificity to the TIMP complexes such as MAC-015 from Cell Tech Lmt. Combinations of antibodies are also contemplated. The monoclonal antibodies can also be prepared using laboratory techniques known to those of ordinary skill in the art, such as that provided by Cooksley, et al. MATRIX 10:285-291, 1990, or from commercial laboratory sources such as Cell Tech Lmt. The antibodies employed in this assay could also react to a new immunogen consisting of peptide components derived from a portion of the TIMP molecule and a portion of the MMP molecule. Likewise, neoantigens could be produced as a result of the complexing of TIMP and MMP, thus resulting in a unique antigen that would be diagnostic of the formation of complexes.

A preferred immunologic means of detecting metalloproteinases is the Enzyme-Linked Immunosorbent Assay (ELISA) method, and in particular the sandwich-type ELISA format. This assay method includes introducing a biological sample between a capture layer of antibodies and a detection layer of antibodies.

In this regard, diagnostic well plates, such as IMMULON II 96 well microtiter plates available from Dynatech, Alexandria, VA, are first coated with capture antibodies directed to MMPs such as rabbit polyclonal antibodies to human 72 kDa gelatinase or 92 kDa progelatinase/type IV procollagenase. The capture antibodies are introduced into the wells in amounts ranging from about 10 $\mu$l to about 200 $\mu$l with amounts %f about 100 $\mu$l being preferred. The capture antibodies are preferably diluted in a suitable buffer such as 0.1 M $NaHCO_3$, pH 9.0 to about 1:200 concentration prior to introduction into the wells.

Binding of the capture antibodies to the well is carried out over a period of from about 4 to about 24 hours and preferably about 18 hours after inoculation at temperatures ranging from about 0 about 10° C. and preferably about 4° C. Unbound antibodies are thereafter removed by vigorously inverting the plates. The wells containing the bound antibodies are next bathed with a bovine serum albumin/bicarbonate buffer to block excess binding sites on the wells. The bottom layer of the "sandwich" or capture layer is completed by washing the plate thoroughly with a buffer solution containing sodium phosphate, sodium chloride and Tween 20.

The ELISA technique further includes introducing a biological sample such as human plasma onto the capture antibody layer. The samples are preferably prepared by being diluted in an incubation-suitable buffer to about a 1:10 concentration. One such solution contains 50 mM sodium phosphate, 0.1 M sodium chloride, 0.02% Tween 20 and 0.1% bovine serum albumin (BSA). The samples are placed in the well, incubated at a temperature ranging from about 25° C to about 37° C, and preferably at about 37° C for a time period of from about 1 hour to about 4 hours and preferably about one hour.

The final part of the ELISA "sandwich" is a detection layer containing an antibody specific to free TIMP-1 or TIMP-2 recognizing TIMP in complexes. The wells containing the capture antibody and sample are washed thoroughly before introducing a detection antibody into the well such as monoclonal murine anti-TIMP-1, anti-TIMP-2 antibodies or the like. The antibodies are preferably added after being diluted in an incubation buffer to a concentration of about 1:4000.

The wells are incubated for about 1 hour and thereafter washed thoroughly and prepared using standard ELISA techniques known to the art, such as including the amplifying goat antibodies to mouse IgG and then alkalinephosphatase conjugated to streptavidin. The wells are then washed and 100 microliters of substrate p-nitrophenyl phosphate in buffer is added to generate a color reaction which is read at $A_{405}$. The results of the assay are obtained using any suitable reading device such as that available from BioTek of Winooski, VT. In addition, the optimal concentration of capture antibodies such as polyclonal rabbit anti-gelatinase A, and detecting antibodies such as monoclonal murine anti-TIMP-1, is determined using checkerboard titration. In this procedure, the concentrations of different antibodies and antigens are varied by serial dilution of the reagents to determine the concentration of each reagent, giving the highest percentage of true positive results and the lowest percentage of false positive results.

While the present invention is not solely limited to ELISA immunological techniques, the ELISA technique is particularly preferred since the method allows the artisan to detect concentrations of a particular substance, in this case MMPs, in nanogram per milliliter concentrations. Other suitable immunological techniques include radioimmunoassay fRIA), Western dot blot, dip stick, zymography as well as immunological techniques known to those of ordinary skill in the art. For example, in certain techniques an absolute-type reading, i.e., a color change, indicates the presence of disease. In a preferred embodiment, a quantitative or numeric value indicating the level of enzyme-complex concentration or activity is provided thereby allowing comparison to a reference standard.

In another aspect of the present invention, a kit is provided for detecting the-presence of metastatic disease in a biological sample. The kit provides the inventive diagnostic agent as described herein and means for measuring the total amount of MMP Complexed with circulating inhibitors thereof. In particular, the kit includes antibodies, preferably monoclonal or polyclonal antibodies against MMPs and a second type of antibody, preferably monoclonal or polyclonal antibodies directed against TIMPs. The means for measuring can be any suitable means known to those of ordinary skill in the art such as antibody coated beads or other solid phase immobilized antibodies. Measuring may also be accomplished by Enzyme Linked Immunosorbent Assay (ELISA)/radio-immunoassay, zymography and the like techniques.

Other immunologic detection means can be readily adapted for use in connection with the diagnostic agent and method of the present invention. It is intended that all such alternative measuring and diagnostic means be included within the scope of the present invention.

With particular regard to the antibodies included herein, it will be appreciated by those of skill in the art that such antibodies, both monoclonal and polyclonal types are available from commercial sources such as Cell Tech Lmt. of Slough, England, or can be prepared using standard laboratory practices.

EXAMPLES

In the Examples set forth below, various aspects of the present invention are set forth to provide further appreciation of the invention. The Examples, however, are not meant in any way to restrict the effective scope of the invention.

EXAMPLE I

Sandwich-type ELISA Immunoassay For Detection of MMP-2 and MMP-2/TIMP-2 Complexes In Human Plasma In this Example a preferred immunoassay is prepared. Initially, 96 well microtiter plates (Dynatech IMMULON II, Alexandria, VA) were coated with 100 µl of polyclonal rabbit anti-TIMP-2 (NIH, Bethesda, MD) diluted to a concentration of 1:200 in 0.1 M NaHCO3, pH 9.0 for 18 hours at 4° C. The unbound anti-TIMP-2 was removed and 200µl of 1% bovine serum albumin in bicarbonate buffer was added twice for 30 minutes at 34° C. to block excess binding sites on the wells. The plate was washed 3 times with a washing buffer containing 50 mM sodium phosphate, pH 7.2, 0.1 M NaCl, 0.05% Tween 20.

Twenty-eight human plasma samples and six 100µl purified MMP-2/TIMP-2 complex standards were each diluted in an incubation buffer containing 50 mM sodium phosphate, pH 7.2, 0.1M NaCl, 0.02% ?ween 20, 0.1% bovine serum albumin, (BSA), and separately added to individual wells for 2 hours at 37° C. The wells were thereafter washed 3 times with washing buffer. Monoclonal murine anti-MMP-2 obtained from the University of Alabama, Birmingham, diluted 1:4000 in incubation buffer, was added in an amount of 100 µl per well. The plates were incubated at 37° C. for 1 hour.

The plates containing the ELISA sandwich were completed by being washed 3 times and adding 100 µl of biotin labeled goat antibodies to mouse IgG, IgA, IgM (H&L chains) in a concentration of 1:1000 before being incubated at 37° C. for 1 hour. The plates were again washed 3 times and alkaline-phosFhatase conjugated to streptavidin (1:1000 dilution, 100 µl ) was added to each well and the plates were incubated for 30 min. at 37° C. The biotin and streptavidin reagents are employed to amplify the signal from the detecting antibody reagent, thus permitting the detection of nanogram per ml concentrations of gelatinase-TIMP complexes. Alkaline phosphatase conjugated to streptavidin is the enzyme used to generate color from the p-nitrophenyl phosphate substrate.

The wells were washed 3 times with PBS-Tween phosphate-buffered saline with ?ween detergent and 3 times with water. 100 µl of substrate p-nitrophenyl phosphate (1mg/ml) in 0.1M glycine, 1 mMMgCl2, 1 mM ZnCl2, pH 10.4 was added and after 30-90 minutes at room temperature, the plates containing both the human plasma samples and the purified standards were read at $A_{405}$ in a Microplate Autoreader (BioTekIEL 309. Winooski, Vt.). Quantification of MMP-2/TIMP-2 complexes was made by extrapolation from a log-log linear regression curve employing varying concentrations of purified MMP-2/TIMP-2 complex as standard. The results are set forth in the Table below and are graphically illustrated in FIG. 1.

TABLE

| DIAGNOSIS | STAGE | MMP-2 (ng/ml) Norm. Conc. = 0-828 | MMP-2/ TIMP-2* (units/ml) Norm. Conc. = 0-694 | MMP-9 (ng/ml) Norm. Conc. = 0-31 |
|---|---|---|---|---|
| CONTROLS | | | | |
| A | | 610 | 288 | 0 |
| B | | 716 | 458 | 14 |
| C | | 677 | 423 | 17 |
| D | | 488 | 277 | 18 |
| E | | 615 | 271 | 8 |
| F | | 823 | 596 | 36 |
| G | | 496 | 556 | 1 |
| H | | 617 | 188 | 1 |
| I | | 1381 | 604 | 25 |
| J | | 633 | 173 | 5 |
| K | | 683 | 434 | 2 |
| L | | 616 | 446 | 0 |
| GI CANCER | | | | |
| A | 3 | 480 | 1429 | 63 |
| B | 3 | 774 | 377 | 4 |
| C | 4 | 591 | 657 | 5 |
| D | 4 | 312 | 406 | 22 |
| E | 4 | 664 | 933 | 126 |
| F | 4 | 658 | 596 | 4 |
| G | 4 | 908 | 3277 | 45 |
| H | 2 | 500 | 779 | 1 |
| BREAST CANCER | | | | |
| A | 4 | 622 | 804 | 1 |
| B | 1 | 734 | 509 | 0 |
| C | 3 | 1145 | 2428 | 51 |
| D | 3 | 759 | 382 | 4 |
| E | 4 | 786 | 2429 | 5 |
| F | 4 | 1226 | 1278 | 71 |
| G | 4 | 687 | 639 | 41 |
| H | 3 | 734 | 593 | — |

Key
*Units/ml based on a reference standard purified from human plasma using gelatin sepharose chromatography followed by gel filtration chromatography.

As shown in the above Table, the normal range was based on the mean±2 S.D. of 12 normal plasma samples collected in EDTA anticoagulant. Four out of eight GI cancer patient specimens and four out of eight breast cancer patient specimens (50%) had significantly increased levels of MMP-2/TIMP-2 complexes. These patients tended to have advanced cancer, indicating that this assay would be predictive of patients with metastatic cancer.

The MMP-2/TIMP-2 complex assay provided results that were independent from isolated measurements of either MMP-2 alone or MMP-9 alone. Some patients had elevations of MMP-2/TIMP-2 complexes and normal levels of MMP-2 or MMP-9, indica that multiple different assays will be supplemental in enhancing the diagnostic utility of these assays. Results of MMP-2 measurements alone have not proven to be useful in the diagnosis of metastatic cancer. Furthermore, it is critical that the blood specimens obtained from patients be anticoagulated such as with EDTA since the levels of MMPs are falsely elevated in serum as a result of release of MMPs especially MMP-9 or gelatinase B from white blood cells during the clotting process.

EXAMPLES II–IX

In these ExamDies, sandwich ELISA assays were prepared in a manner similar to that set forth in Example I, except that the capture and detection antibodies were varied so that different matrix metalloproteinases could be detected. The various combinations of immunoassay detection systems provide the clinician with a battery of diagnostic assays useful in the identification, diagnosis, treatment and determination of prognosis in patients with various types of cancer. The illustrative assays are set forth below.

| EXAMPLE | II | III | IV | V | VI | VII | VIII | IX |
|---|---|---|---|---|---|---|---|---|
| CAPTURE ANTIBODY TO DETECT TIMP SHOWN | TIMP-1 | TIMP-1 | TIMP-2 | TIMP-1 | TIMP-2 | TIMP-2 | TIMP-2 | TIMP-1 |
| DETECTION ANTIBODY TO DETECT MMP SHOWN | MMP-9 | MMP-3 | MMP-3 | MMP-1 | MMP-1 | MMP-2 | MMP-9 | MMP-2 |

The above assays can be combined with other diagnostic methods such as (CEA) carcinoembroyonic antigen measurements useful for colon cancer diagnosis and CA-125 (useful in ovarian cancer diagnosis) as a further or confirmational indicator of tumor growth and/or metastatic disease. It is to be understood that the above-listed combinations are illustrative and in no way represent the complete range of possible assays which can be prepared in accordance with the present invention.

EXAMPLE X

In this Example, a sandwich ELISA format immunoassay was prepared in a manner such as that set forth in Example I. The assay in this Example, however, contained mouse monoclonal antibodies to human TIMP-1 MAC-015 antibody from Cell Tech Lmt. to capture TIMP-1/MMP-9 complexes and biotinylated monoclonal mouse antibodies to 92 kDa matrix metalloproteinases prepared according to the method set forth by Bergmann, et al. supra, the disclosure of which is incorporated by reference herein. The assay was used to compare the levels of these complexed antigens present in the plasma of patients with various types of cancer with those of non-cancerous controls. The cancer group was further defined as patients with gastrointestinal cancers (GI) and patients with female genitourinary tract (GU) cancers such as cancers of the ovary, cervix, vagina and uterus. The results are set forth in the Table below.

TABLE

| GROUP n = sample size | MMP-9/ TIMP-1 COMPLEX INCREASE ONLY DETECTED | MMP-9 INCREASE ONLY DETECTED | MMP-9/ TIMP-1 COMPLEX AND MMP-9 INCREASE DETECTED | TOTAL NUMBER OF POSITIVES (%) |
|---|---|---|---|---|
| Controls n = 49 | 1 | 1 | 1 | 3 (6%) |
| GI cancer n = 94 | 14 | 14 | 7 | 35 (37%) |
| GU cancer n = 23 | 8 | 3 | 4 | 15 (65%) |

Referring now to the Table, it can be clearly seen that there are significant analytical advantages in measuring the levels of MMP complexes in addition to free MMPs to detect or confirm metastatic disease.

The above data dramatically illustrate this point for patients with GU cancer. Consider that by measuring only MMP-9, the clinician was able to confirm the presence of metastatic disease in only 3 of 23 (13%) known metastatic plasma samples. However, when the clinician also assays complexes of the enzyme and combinations of free enzymes and complexes, the summation of all assays provides a much more accurate diagnostic indicator. Moreover, the data obtained from measuring TIMP/MMP complexes is independent from that obtained by measuring MMP-9 assays alone. The present invention, therefore, provides supplemental information regarding metastatic disease. Patients with other types of cancer may have elevations of different types of MMP complexes thus necessitating the performance of a battery of different tests such as that set forth in Examples II-IX to optimize the diagnostic potential of detecting aggressive cancer at an earlier stage.

The above Example provides further evidence of a strong link between the invasive/metastatic process and the increased levels of metalloproteinases, both free and with inhibitor complexes in human plasma. Moreover, there is also a positive correlation between highly metastatic cancer cell lines (phenotypes) and increased secretion of certain enzyme complexes. The practitioner, therefore, can custom tailor the assay, for example, by substituting capture and detection antibodies to measure specific antigens. It is contemplated that assays for specific metastatic diseases such as breast and/or gastrointestinal cancers could be developed based on the results obtained from subjecting a biological sample to a battery of specific antibodies.

While there have been described what are presently believed to be the preferred embodiments of the invention, those skilled in the art will realize that changes and modifications may be made thereto without parting from the spirit of the invention, and it is intended to claim all such changes and modifications as fall within the true scope of the invention.

What is claimed is:

1. A method of screening for the presence of metastic disease in a biological sample, comprising:
   a) contacting a biological sample with a first immunologically responsive substance which specifically binds a molecule selected from a first group consisting of matrix metalloprateinase, matrix metalloproteinase complexed with tissue inhibitor of metalloproteinase, and break down products thereof; or a second group consisting of tissue inhibitor of metalloproteinase, tissue inhibitor of metalloproteinase complexed with matrix metalloproteinase and break down products thereof;

b) isolating a product having said first immunologically responsive substance that may be bound to said biological sample;

c) contacting said product with a second detactably labled immunologically responsive substance which specifically binds a molecule selected from said first group or from said second group wherein, if said first immunologically responsive substance is selected from said first group then said second immunologically responsive substance is selected from said second group, or if said first immunologically responsive substance is selected from said second group then said second immunologiclly responsive substance is selcted from said first group;

d) detecting said second detectably labeled immunologically responsive substance;

e) quantifying an amount of said second detectably labeled immunologically responsive substance detected in step d);

f) comparing said amount with a reference standard of metastatic disease to provide a quantitative value; and g) correlating said quantitative value to metastatic disease in said biological sample.

2. The method of claim 1, wherein step a) comprises: contacting said biological sample with said first immunologically responsive substance which specifically binds a molecule selected from asid first group further consisting of 72 kDa type IV collagenase/gelatinase A (MMP-2), 92 kDa type IV collagenase/gelatinase B (MMP-9) stromelysin (MMP-3), putative metalloproteinase (PUMP), break down products and mixtures thereof; or said second group further consisting of tissue inhibitor of metalloproteinase (TIMP-1), tissue inhibitor of metalloproteinase (TIMP-2) and alpha-2 macroglobulin, break down products and mixtures thereof.

3. The method of claim 1, wherein step c) further comprises contacting said product with said second detectably labeled immunologically responsive substance which is labeled with a detectable substance selected from the group consisting of biotin, radioactive agents, chromophoric agents and enzymatic agents.

4. The method of claim 1, wherein detecting said second detectably labeled immunologically responsive subsance in step d) is accomplished utilizing a detection method selected from the group consisting of an enzyme linked immunosorbent assay, an immunoassay, a radio-immunoassay and zymography.

5. The method of claim 11, whrein quantifying said amount of said detectably labeled immunologically responsive substance recited in step e) is accomplished utilizing a quantification method selected from the group consisting of quantifying electro-magnetic absorbance and radioactive emissions.

6. The method of claim 1, wherein correlating said quantitative value to metastatic disease in said biological sample recited in step g) is accomplished utilizing a correlation method selected from the group consisting of log-log linear regression and color change.

7. The method of claim 1, wherein said first immunologically responsive substance is contacted in an amount from about 0.01 ng/ml to about 2000 ng/ml by weight of said biological sample and said second immunologically responsive substance is contacted in an amount from about 0.01 ng/ml to about 2000 ng/ml by weight of said biological sample.

8. A method of screening for the presence of metastatic disease in a biological sample, comprising:

a) contacting a biological sample with a detectably labeled immunologically responsive substance which specifically binds a matrix metalloproteinase-tissue inhibitor of metalloproteinase complex and break down products thereof;

b) detecting said detectably labeled immunologically responsive substance bound to said biological sample;

c) quantifying an amount of said detectably labeled immunologically responsive substance detected in step b);

d) comparing said amount with a reference standard of metastatic disease to provide a quantative value; and e) correlating said quantitative value to metastatic disease in said biological sample.

9. The method of claim 8, wherein detecting said detectably labeled immunologically responsive substance in step a) is accomplished utilizing a detection method selected fro the group consisting of an enzyme linked immunosorbent assay, an immunoassay, a radio-immunoassay and zymography.

10. The method o claim 8, wherein quantifying said amount of said detectably labeled immunologically responsive substance recited in step c) is accomplished utilizing a quantitation method selected from the group consisting of quantifying electro-magnetic absorbance and radioactive emissions.

11. The method of claim 8, wherein correlating said quantitative value to metastatic disease in said biological sample recited in step c) is accomplished utilizing a correlation method selectded frm the group consisting of log-log linear regression and color change.

* * * * *